United States Patent

Petersen et al.

[11] Patent Number: 5,859,010
[45] Date of Patent: Jan. 12, 1999

[54] FACTOR VII -BINDING REAGENT

[75] Inventors: Lars Christian Petersen, Horsholm; Ole Hvilsted Olsen, Bronshoj; Stefan Lutz Richter, Gentofte; Palle Jakobsen, Vaerlose, all of Denmark

[73] Assignee: Novo Nordisk A/S, Bagsvaerd, Denmark

[21] Appl. No.: 880,699

[22] Filed: Jun. 23, 1997

[30] Foreign Application Priority Data

Jun. 24, 1996 [DK] Denmark .................................. 0696/96

[51] Int. Cl.⁶ ...................... A61K 31/495; C07C 251/00; C07C 251/34; C07D 241/36
[52] U.S. Cl. ........................... 514/249; 514/507; 514/508; 514/740; 544/354; 562/622; 564/123; 564/229
[58] Field of Search ............................... 544/354; 514/249

[56] References Cited

U.S. PATENT DOCUMENTS

| | | | |
|---|---|---|---|
| 5,514,680 | 5/1996 | Weber et al. | 514/249 |
| 5,639,739 | 6/1997 | Dominguez et al. | 514/64 |
| 5,693,515 | 12/1997 | Clark et al. | 435/184 |

FOREIGN PATENT DOCUMENTS

| | | |
|---|---|---|
| 0 377 112 | 7/1990 | European Pat. Off. . |
| WO 94/24096 | 10/1994 | WIPO . |

OTHER PUBLICATIONS

Koshti et al., Tetrahedron Letters, vol., 35 No. 29, pp. 5157–5160 (1994).
Farkas et al., Chemical Abstracts, vol. 118, No. 8, p. 532 (Feb. 22, 1993).

*Primary Examiner*—Johann Richter
*Assistant Examiner*—Jane C. Osweki
*Attorney, Agent, or Firm*—Steve T. Zelson, Esq.; Valeta Gregg, Esq.

[57] ABSTRACT

The invention relates to novel compounds that potentiate zinc ion inhibition of the activity of factor VIIa or tissue factor—factor VIIa complex having the formula Ia and Ib and pharmaceutical salts thereof as well as pharmaceutical compositions comprising said novel compounds. The invention is further related to the use of said compositions for inhibiting clotting activity, tissue factor activity and factor VIIa activity.

20 Claims, 4 Drawing Sheets

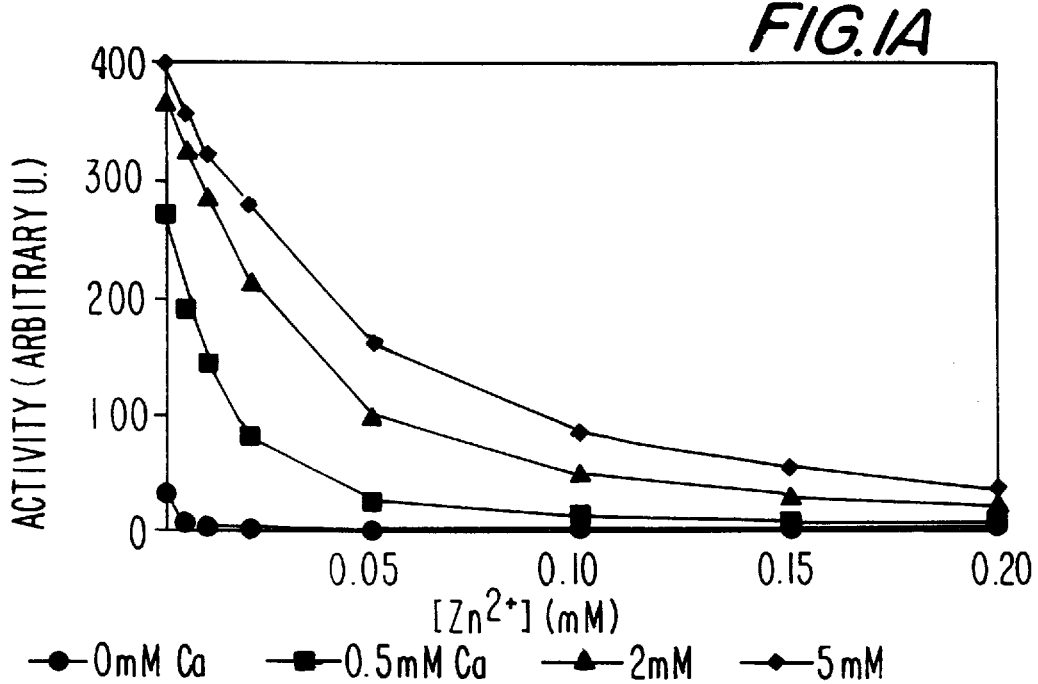
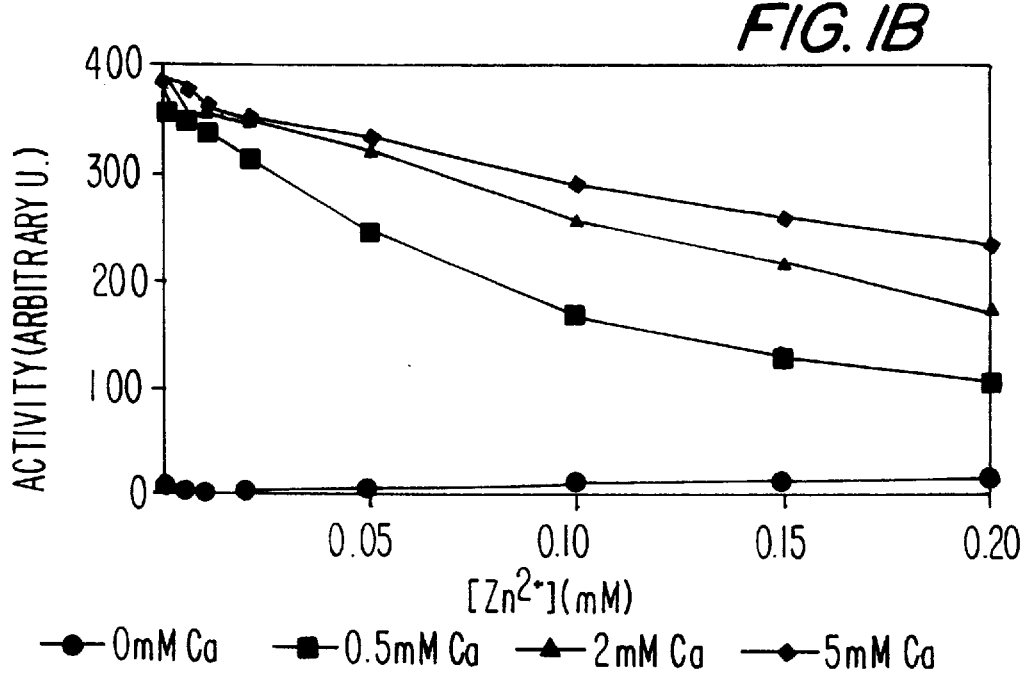

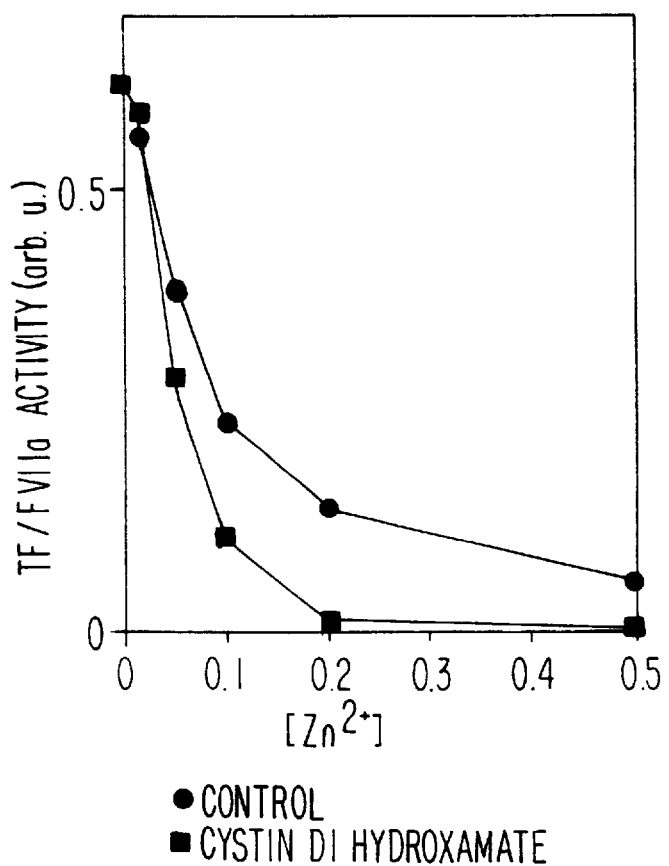

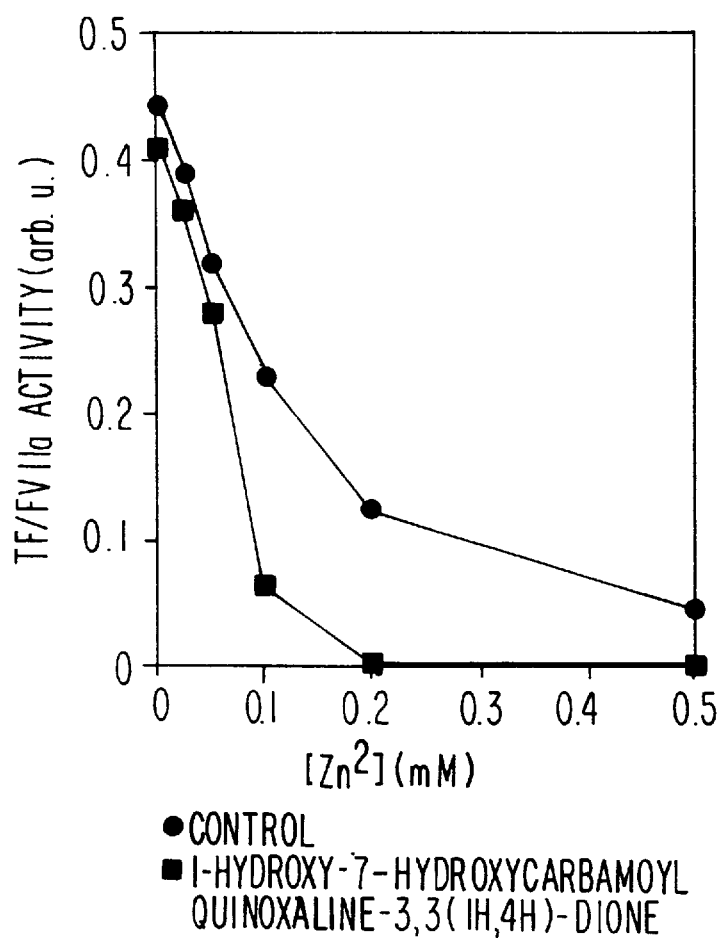

FACTOR VII-BINDING REAGENT

CROSS-REFERENCE TO RELATED APPLICATIONS

This application claims priority under 35 U.S.C. 119 of Danish application 0696/96 filed Jun. 24, 1996, the contents of which are fully incorporated herein by reference.

FIELD OF INVENTION

The present invention relates to reagents useful as anticoagulants. More specifically, the invention relates to novel compounds that potentiates zinc ion inhibition of the activity of factor VIIa or tissue factor-factor VIIa complex, and pharmaceutical salts thereof. The invention further relates to pharmaceutical compositions, the preparation hereof, the use of the compounds of formula Ia and Ib as inhibitors of clotting activity, and methods of inhibiting clotting activity, tissue factor activity, and FVIIa activity.

BACKGROUND OF INVENTION

Blood coagulation is a process consisting of a complex interaction of various blood components, or factors, which eventually gives rise to a fibrin clot. Generally, the blood components which participate in what has been referred to as the coagulation "cascade" are proenzymes or zymogens, enzymatically inactive proteins, which are converted to proteolytic enzymes by the action of an activator, itself an activated clotting factor. Coagulation factors that have undergone such a conversion and generally referred to as "active factors", and are designated by the addition of the letter "a" to the name of the coagulation factor (e.g. factor VIIa).

Activated factor X ("Xa") is required to convert prothrombin to thrombin, which then converts fibrinogen to fibrin as a final stage in forming a fibrin clot. There are two systems, or pathways that promote the activation of factor X. The "intrinsic pathway" refers to those reactions that lead to thrombin formation through utilisation of factors present only in plasma. A series of protease-mediated activations ultimately generates factor IXa, which, in conjunction with factor VIIIa, cleaves factor X into Xa. An identical proteolysis is effected by factor VIIa and its co-factor, tissue factor, in the "extrinsic pathway" of blood coagulation. Tissue factor is a membrane bound protein and does not normally circulate in plasma. Upon vessel wall injury, however, it is exposed and forms a complex with factor VIIa to catalyse factor X activation or factor IX activation in the presence of $Ca^{++}$ and phospholipid (Nemerson and Gentry, *Biochem.* 25:4020–4033 (1986)). While the relative importance of the two coagulation pathways in hemostasis is unclear, in recent years factor VII and tissue factor have been found to play a pivotal role in the initiation and regulation of blood coagulation.

Factor VII is a trace plasma glycoprotein that circulates in blood as a single-chain zymogen. The zymogen is catalytically inactive (Williams et al., *J. Biol. Chem.* 264:7536–7543 (1989); Rao et al., *Proc. Natl. Acad. Sci. USA.* 85:6687–6691 (1988)). Single-chain factor VII may be converted to two-chain factor VIIa by factor Xa, factor XIIa, factor IXa, factor VIIa or thrombin in vitro. Factor Xa is believed to be the major physiological activator of factor VII. Like several other plasma proteins involved in hemostasis, factor VII is dependent on Vitamin K for its activity, which is required for the gamma-carboxylation of multiple glutamic acid residues that are clustered in the amino terminus of the protein. These gamma-carboxylated glutamic acids are required for the metal-associated interaction of factor VII with phospholipids.

The conversion of zymogen factor VII into the activated two-chain molecule occurs by cleavage of an internal $Arg_{152}$-$Ile_{153}$ peptide bond (Hagen et al., *Proc. Natl. Acad. Sci. USA* 83: 2412–2416 (1986); Thim et al., *Biochem.* 27:7785–7793 (1988) both of which are incorporated herein by references). In the presence of tissue factor, phospholipids and calcium ions, the two-chain factor VIIa rapidly activates factor X or factor IX by limited proteolysis.

Divalent cations profoundly affect factor VIIa activity. Factor VIIa requires $Ca^{2+}$-ions and tissue factor for optimal activity. Apparently $Ca^{2+}$ is required for binding to tissue factor as well as for induction of an active conformation of the FVIIa molecule. $Zn^{2+}$-ions have been shown to inhibit FVIIa activity, (Pedersen, et al.,: *Thromb. Haemostas.* 65:528–534 (1991); the normal concentration of free $Zn^{2+}$-ions in the blood (15 $\mu$M) being 4–10 fold lower than the apparent Ki for zinc inhibition. It was suggested by these investigations that a histidine residue at position 241 immediately adjacent to the active site might be involved in coordination of the inhibitory $Zn^{2+}$-ion.

It is often desirable to selectively block or inhibit the coagulation cascade in a patient. Anticoagulants such as heparin, coumarin, derivatives of coumarin, indandione derivatives, thrombin inhibitors, factor Xa inhibitors, modified factor VII or other agents may be used.

Inhibition of coagulation is beneficial in a number of diseased states, for example during kidney dialysis, or to treat deep vein thrombosis, disseminated intravascular coagulation (DIC), and a host of other medical disorders. For example, heparin treatment or extracorporeal treatment with citrate ion (U.S. Pat. No. 4,500,309) may be used in dialysis to prevent coagulation during the course of treatment. Heparin is also used in preventing deep vein thrombosis in patients undergoing surgery. Treatment with heparin and other anticoagulants may, however, have undesirable side effects. Available anticoagulants generally act throughout the body, rather than acting specifically at a clot site. Heparin, for example, may cause heavy bleeding. Furthermore, with a half-life of approximately 80 minutes, heparin is rapidly cleared from the blood, necessitating frequent administrating. Because heparin acts as a cofactor for antithrombin III (AT III), and AT III is rapidly depleted in DIC treatment, it is often difficult to maintain the proper heparin dosage, necessitating continuous monitoring of AT III and heparin levels. Heparin is also ineffective if AT III depletion is extreme. Further, prolonged use of heparin may also increase platelet aggregation and reduce platelet count, and has been implicated in the development of osteoporosis. Indandione derivatives may also have toxic side effects.

Other known anticoagulants comprise Thrombin- and factor Xa inhibitors derived from bloodsucking organisms. Antithrombins, Hirudin, Hirulog and Hirugen are recombinant proteins or peptides derived from the leach *Hirudo medicinalis* whereas the factor Xa inhibitor antistatin and the derivative rTAP are tick-derived recombinant proteins. Inhibitors of platelet aggregation such as monoclonal antibodies or synthetic peptides, which interfere with platelet receptor GPIIG/IIIa are also effective as anticoagulants.

Bleeding complications are observed as an unwanted major disadvantage of antithrombin, antifactor Xa, as well as antiplatelet reagents. This side effect is strongly decreased or absent with inhibitors of the factor VIIa/TF activity. Such anticoagulants comprise the physiological inhibitor TFPI (tissue factor pathway inhibitor) and modified factor VII (FVIIai), which is factor VII modified in such a way that it is catalytically inactive, but still binds to TF and compete with active factor VIIa.

In addition to the anticoagulants briefly described above, several naturally occurring proteins have been found to have anticoagulant activity. For example, Reutelingsperger (U.S. Pat. No. 4,736,018) isolated anticoagulant proteins from bovine aorta and human umbilical vein arteries. Maki et al. (U.S. Pat. No. 4,732,891) disclose human placenta-derived anticoagulant proteins. In addition, AT III has been proposed as a therapeutic anticoagulant (Schipper et al., Lancet 1 (8069): 854–856 (1978); Jordan, U.S. Pat. No. 4,386,025; Bock et al., U.S. Pat. No. 4,517,294).

Proliferation of smooth muscle cells (SMCs) in the vessel wall is an important event in the formation of vascular lesions in atherosclerosis, after vascular reconstruction or in response to other vascular injury. For example, treatment of atherosclerosis frequently includes the clearing of blocked vessels by angioplasty, endarterectomy or reduction atherectomy, or by bypass grafting, surgical procedures in which atherosclerotic plaques are compressed or removed through catheterization (angioplasty), stripped away from the arterial wall through an incision (endarterectomy) or bypassed with natural or synthetic grafts. These procedures remove the vascular endothelium, disturb the underlying intimal layer, and result in the death of medial SMCs. This injury is followed by medial SMC proliferation and migration into the intima, which characteristically occurs within the first few weeks and up to six months after injury and stops when the overlying endothelial layer is re-established. In humans, these lesions are composed of about 20% cells and 80% extracellular matrix.

In about 30% or more of patients treated by angioplasty, endarterectomy or bypass grafts, thrombosis and/or SMC proliferation in the intima causes re-occlusion of the vessel and consequent failure of the reconstructive surgery. This closure of the vessel subsequent to surgery is known as restenosis.

Modified factor VIIa (FVIIai) has been shown to effectively suppress the restenosis process possibly as a result of a decreased clot formation and thrombin generation initially after treatment of the constricted vessel.

There is still a need in the art for improved compositions having anticoagulant activity which can be administered at relatively low doses and do not produce the undesirable side effects associated with traditional anticoagulant compositions. The present invention fulfils this need by providing anticoagulants that act specifically at sites of injury, and further provides other related advantages such as its effect on the restenosis process. As compared to other anticoagulants with an effect at factor VIIa/TF activity the present invention has the additional advantage that it is a small synthetic molecule suitable for oral administration and for prophylactic treatment of atherosclerotic patients at risk for thrombosis.

It has now surprisingly been found that $Zn^{2+}$-ions exert their inhibitory action in competition with a stimulatory effect of $Ca^{2+}$-ions. It is predicted that $Zn^{2+}$-ions displace $Ca^{2+}$-ions from the calcium binding site believably located in the serine protease domain of FVIIa. The actual site involved is believed to be a Ca site located in a loop of the serine protease domain comprising residues 208–222 of FVIIa (Wildgoose, et al., Biochemistry 32, 114–119(1993); Banner et al. Nature 380:41–46(1996)). This site is located on top of the substrate binding pocket (active site) of the active FVIIa molecule (FIG. 4).

Zinc is very unusual as a ligand for proteases of the chymotrypsin-like serine protease family, to which factor VII belongs. However, zinc is required for catalysis as an obligatory constituent of the active site of another class of proteolytic enzymes, the metalloproteases.

International Patent Publications Nos. WO95/19957, WO92/09563, WO92/09556, WO95/29892, WO95/06031, and WO93/20047 disclose inhibition of several metalloproteinases using hydroxamate-type compounds. These proteases comprise e.g. thermolysin, stromeolysin, collagenase, gelatinase, carboxypeptidases, angiotensin converting enzyme, matrilysin, and enkephalinases. The used hydroxamates provides a bidentate ligand to an essential zinc atom required for catalysis located within the active site and thus blocks proteolysis (Browner et al. Biochemistry 34:6602–6610(1995).

With factor VII it has now surprisingly been found that certain compounds e.g. hydroxamates and hydrazides are capable of acting as powerfull supporters for binding of zinc ions in competition with calcium ions. Thereby specific compounds potentiate zinc inhibition of the activity of the factor VIIa/tissue factor complex. These compounds thus potentiating the inhibition of FVIIa/TF are e.g. dihydroxamates having a spacing from about 0.37 nm to about 0.77 nm, such as 0.57 nm to about 0.67 nm (about 5.7 Angstrom to about 6.7 Angstrom) between their hydroxamate groups.

The mechanism of action for the potentiation of zinc inhibition of FVIIa/TF is thus fundamentally different from the inhibition of metalloproteinases.

SUMMARY OF THE INVENTION

It has surprisingly been found that the activity of factor VIIa alone or in complex with tissue factor can be inhibited by a mechanism in which a zinc chelator binds to factor VIIa and facilitates replacement of $Ca^{2+}$ with $Zn^{2+}$ in the protease domain. By this action the stimulatory effect of $Ca^{2+}$ is replaced by an inhibitory effect of $Zn^{2+}$ preferable to an extent which allows a modulatory effect of the chelator at the normal concentration of free $Ca^{2+}$ and $Zn^{2+}$ ions in the blood.

In particular it has been found that zinc chelators of the general formula Ia or Ib have interesting pharmacological properties. For example, the compounds of this invention can be used in the treatment of deficiencies of blood clotting factors or the effect of inhibitors to blood clotting factors in mammals.

Thus, in one embodiment the present invention concerns the use of compounds having the general formula Ia

 (Ia)

wherein
$M^1$, $M^2$, $Y^1$, $Y^2$, A, p, a and s are as defined below;
or a pharmaceutically acceptable salt thereof,
with the provisos that a+p+s is at least 1.

Each of the above carbon atoms $C_1$ and $C_2$, in formula Ia, are numbered so as to identify the specific carbon atom and shall not indicate anything else.

In another embodiment of the present invention the compounds have the general formula Ib

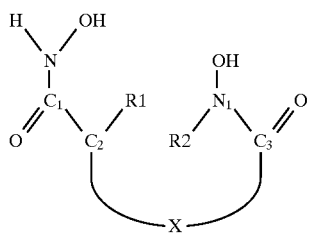

wherein X, R1 and R2 are as defined below;
and wherein the distance between C1 and C3 is from about 0.37 nm to 0.77 nm, e.g. 0.57 nm to about 0.67 nm;
and pharmaceutically acceptable salts thereof;
with the proviso that the compound is not L-cystine dihydroxamate.

Each of the above carbon atoms $C_1$, $C_2$ and $C_3$, in formula Ib, are numbered so as to identify the specific carbon atom and shall not indicate anything else.

BRIEF DESCRIPTION OF THE DRAWINGS

FIG. 1 shows the effect of zinc and calcium ions on the activity of factor VIIa (A) or the factor VIIa-tissue factor complex (FVIIa-TF complex) (B).

FIG. 2 shows the effect of zinc ions on TF-stimulated FVIIa activity in the absence and presence of cystin dihydroxamate. (compound II)

FIG. 3 shows the effect of zinc ions on TF-stimulated FVIIa activity in the absence and presence of 1-hydroxy-7-hydroxycarbamoyl quinoxaline-3,3(1H,4H)-dione (compound II).

DETAILED DESCRIPTION OF THE INVENTION

Figure 4:
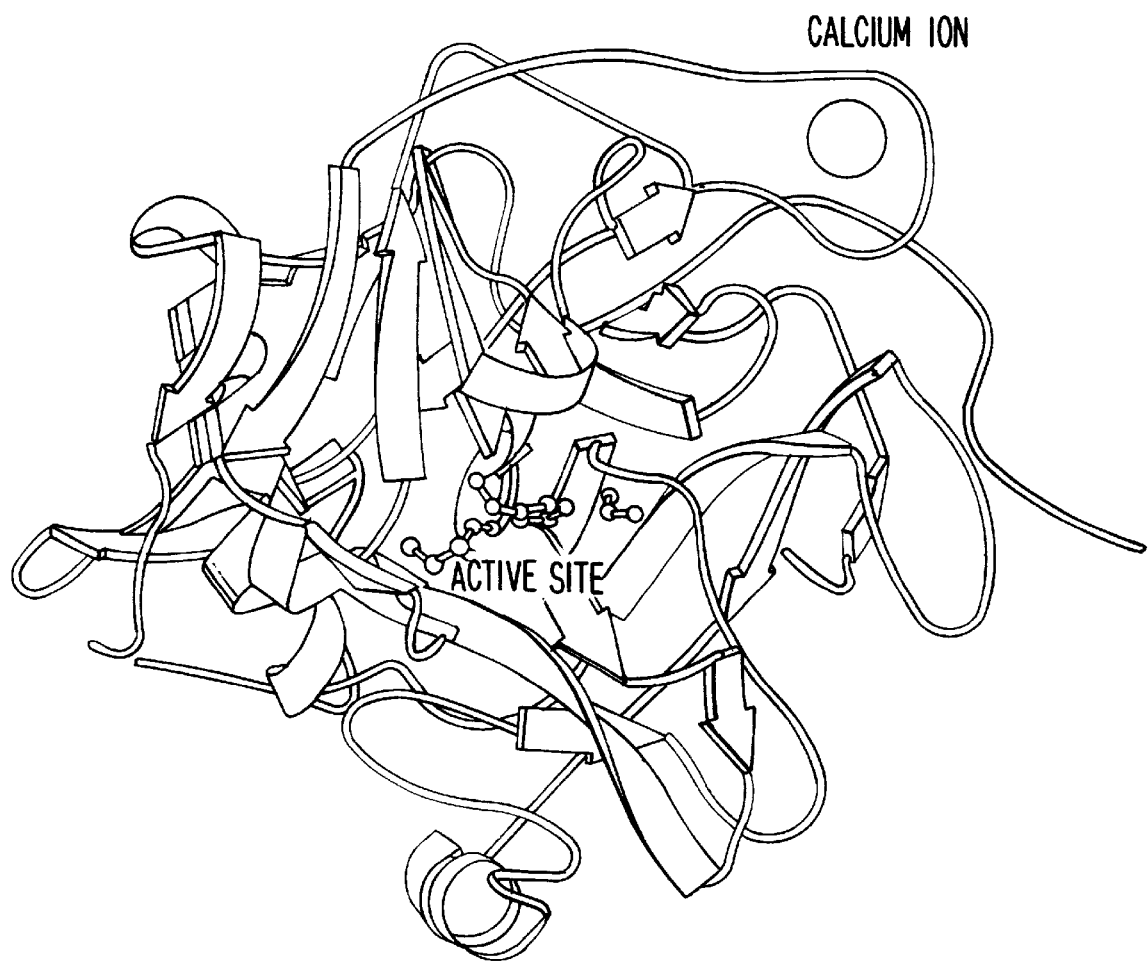
FIG. 4 shows the location of tissue factor binding region, the substrate binding pocket, and the calcium binding site in factor VII.

It has surprisingly been found that the activity of factor VIIa alone or in complex with tissue factor can be inhibited by a mechanism in which a zinc chelator binds to factor VIIa and helps replace $Ca^{2+}$ with $Zn^{2+}$ in the protease domain. By this action, the stimulatory effect of $Ca^{2+}$ is replaced by an inhibitory effect of $Zn^{2+}$ preferably to an extent which allows a modulatory effect of the chelator at the mormal concentration of $Ca^{2+}$ and $Zn^{2+}$ in the blood. Thereby zinc ion inhibition of the activity of factor VIIa alone or in complex with tissue factor is potentiated.

In a first aspect the present invention relates to a compound (zinc chelator) that potentiates zinc ion inhibition of the activity of factor VIIa or tissue factor-factor VIIa complex, with the proviso that the compound is not L-cystine dihydroxamate, 4,7-Dihydro-[4,7]phenanthroline-1,2,3,8,9,10-hexaone-2,9-dioxime, 1,2,3-triazole-4,5-dicarbohydrazide and 5-(2-pyridyl)-1,2,4-triazole-3-carbohydrazide. Thereby the zinc chelator induces inhibition of blood coagulation. In one embodiment the compound is a non-peptide.

Throughout this specification L-cystine dihydroxamate means a compound of the formula

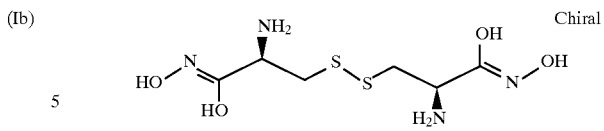

or (due to resonans) the formula

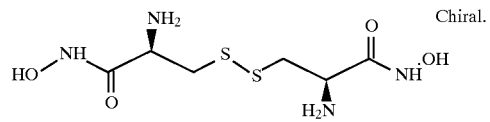

In a second aspect the present invention relates to a compound (zinc chelator) that potentiates zinc ion inhibition of the activity of factor VIIa or tissue factor—factor VIIa complex said compound being characterized by inhibiting factor VIIa or tissue factor—factor VIIa complex in the assay disclosed in example 4, with the proviso that the compound is not L-cystine dihydroxamate, 4,7-Dihydro-[4,7]phenanthroline-1,2,3,8,9,10-hexaone-2,9-dioxime, 1,2,3-triazole-4,5-dicarbohydrazide and 5-(2-pyridyl)-1,2,4-triazole-3-carbohydrazide. Thereby the zinc chelator induces inhibition of blood coagulation. In one embodiment the compound is a non-peptide.

In a third aspect the present invention relates to a compound that binds to factor VIIa and induces replacement of calcium ions with zinc ions in the serine protease domain of factor VIIa, thereby inhibiting the activity of factor VIIa or tissue factor—factor VIIa complex, said compound being characterized by inhibiting factor VIIa or tissue factor—factor VIIa complex in the assay disclosed in example 4, with the proviso that the compound is not L-cystine dihydroxamate, 4,7-Dihydro-[4,7]phenanthroline-1,2,3,8,9, 10-hexaone-2,9-dioxime, 1,2,3-triazole-4,5-dicarbohydrazide and 5-(2-pyridyl)-1,2,4-triazole-3-carbohydrazide. Thereby the zinc chelator induces inhibition of blood coagulation. In one embodiment the compound is a non-peptide. In another embodiment the compound binds to a site located in the serine protease domain of factor VIIa, wherein said site is the calcium site located in a loop of the serine protease domain comprising amino acid residues 208–222 of factor VIIa.

In a preferred embodiment of the first, second or third aspect of the invention, the compound has the formula III

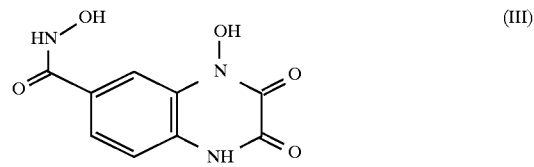

or the formula (IV)

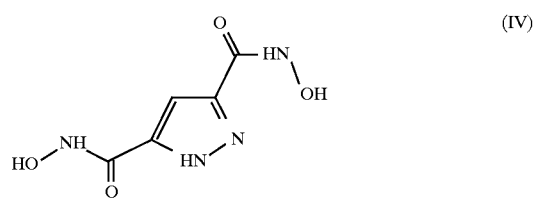

In another embodiment of the first, second or third aspect of the invention it relates to compounds of the general formula Ib

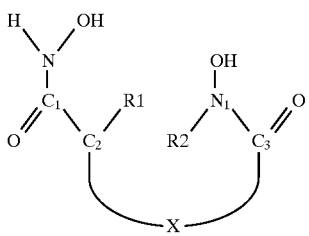

wherein

X is a chain, aliphatic or comprising hetero atoms as chain members;

and R1 is hydrogen, an amino group (optionally substituted with methyl), or a methyl group; and R2 is hydrogen, or a methyl group;

or X, in combination with C2, R1, R2, N1, and C3, forms a carbocyclic or heterocyclic system;

and wherein the distance between C1 and C3 is from about 0.37 nm to about 0.77 nm;

and pharmaceutically acceptable salts thereof.

The residue X may be a branched or unbranched carbon chain, or X may comprise carbon and/or nitrogen and/or sulphur and/or oxygen atoms (chain links) arranged in a branched or unbranched chain. Furthermore, X may comprise single and/or double bonds between chain links. X may also in combination with C2, R1, R2, N1, and C3 form a carbocyclic or heterocyclic system. This system may be monocyclic, bicyclic, or polycyclic with the proviso that the distance between the carbon atoms of the hydroxamate carbonyl groups (C1 and C3 in formula I) is from about 0.37 nm to about 0.77 nm.

In a further embodiment of the compound of general formula Ib, the distance between $C_1$ and $C_3$ is from about 0.37 nm to about 0.47 nm.

In a still further embodiment of the compound of general formula Ib, the distance between $C_1$ and $C_3$ is from about 0.47 nm to about 0.57 nm.

In a further embodiment of the compound of general formula Ib, the distance between $C_1$ and $C_3$ is from about 0.57 nm to about 0.67 nm.

In a still further embodiment of the compound of general formula Ib, the distance between $C_1$ and $C_3$ is from about 0.67 nm to about 0.77 nm.

In a further embodiment of the compound of general formula Ib the distance between $C_1$ and $C_3$ is from about 0.37 nm to about 0.77 nm, preferably from about 0.40 nm to about 0.70 nm, more preferred from about 0.40 nm to about 0.65 nm.

In a preferred embodiment of the compound of formula Ia the compound has the formula III

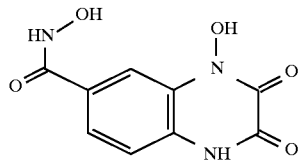

The compounds according to this invention e.g. such compounds having the general formulas Ia or Ib have interesting pharmacological properties. For example, the compounds of this invention can be used to modulate and normalize an impaired haemostatic balance in mammals caused by deficiency or malfunction of blood clotting factors or their inhibitors. The factor VIIa and in particular the factor VIIa/tissue factor activity plays an important role in the control of the coagulation cascade, and modulators of this key regulatory activity such as the present invention can be used in the treatment of coagulation-related diseased states.

In a fourth aspect the present invention relates to a pharmaceutical composition comprising a compound according to the first, second or third aspect of the invention, in combination with a pharmaceutical acceptable excipient and/or carrier. In one embodiment hereof such compound is selected from 1-hydroxy-7-hydroxycarba-moylquinoxaline-2,3(1H,4H)-dione or Pyrazole-3,5-dicarbohydroxamic acid.

In one embodiment of the fourth aspect of the invention, the composition further contains zinc ions. Throughout this specification such zinc ions are meant to comprise the divalent cations, $Zn^{2+}$. Such zinc ions may be provided via zinc salts, e.g. $ZnCl_2$ or the like.

In a further embodiment of the fourth aspect of the invention the pharmaceutical composition is administered by the oral route. However, the route of administration of the compositions containing a compound of the invention may be any route which effectively transports the active compound to its site of action, such as transdermal, pulmonal, subcutane, rectal, etc.

The pharmaceutical composition according to the fourth aspect of the invention may be useful for modulating and normalizing an impaired haemostatic balance in a mammal. In particular, the pharmaceutical composition may be useful for the treatment of coagulation-related diseased states. More particularly the pharmaceutical composition may be useful as an inhibitor of blood coagulation in a mammal, as an inhibitor of clotting activity in a mammal, as an inhibitor of deposition of fibrin in a mammal, as an inhibitor of platelet deposition in a mammal, in the treatment of mammals suffering from deep vein thrombosis, pulmonary embolism, stroke, disseminated intravascular coagulation (DIC), vascular restenosis, platelet deposition and associated disorders and myocardial infarction, and in the prophylactic treatment of mammals with atherosclerotic vessels at risk for thrombosis.

Throughout this specification the term mammal is also intended to comprise a human.

In a fifth aspect the present invention relates to use of a compound according to the first, second or third aspect of the invention for the preparation of a pharmaceutical composition for modulating and normalizing an impaired haemostatic balance in a mammal. In particular, the invention relates to use of a compound according to the first, second or third aspect of the invention for the preparation of a pharmaceutical composition for treatment of coagulation-related diseased states.

In further embodiments of the fifth aspect it is for use as an inhibitor of blood coagulation in a mammal, or for use as an inhibitor of clotting activity in a mammal, or for use as an inhibitor of deposition of fibrin in a mammal, or for use as an inhibitor of platelet deposition in a mammal.

In a still further embodiment of the fifth aspect it relates to use of a compound according to the first, second or third aspect of the invention for the preparation of a pharmaceutical composition, for treatment of mammals suffering from deep vein thrombosis, pulmonary embolism, stroke, disseminated intravascular coagulation (DIC), vascular restenosis, platelet deposition and associated disorders and myocardial infarction, and in the prophylactic treatment of mammals with atherosclerotic vessels at risk for thrombosis.

In a further embodiment of the fifth aspect the composition further contains zinc ions.

In a sixth aspect the invention relates to a method of modulating and normalizing an impaired haemostatic balance in a mammal, which method comprises administering an effective amount of a compound according to the first, second or third aspect of the invention, optionally in combination with a pharmaceutical acceptable excipient and/or carrier to the mammal in need of such a treatment. Such compound being e.g. 1-hydroxy-7-hydroxycarbamoylquinoxaline-2,3(1H,4H)-dione or Pyrazole-3,5-dicarbohydroxamic acid. In one embodiment the method further comprises administering zinc ions.

The present invention also relates to a method for treatment of coagulation-related diseased states in a mammal, which method comprises administering an effective amount of a compound according to the first, second or third aspect of the invention, optionally in combination with a pharmaceutical acceptable excipient and/or carrier to the mammal in need of such a treatment. Such compound being e.g. 1-hydroxy-7-hydroxycarbamoylquinoxaline-2,3(1H,4H)-dione or Pyrazole-3,5-dicarbohydroxamic acid. In one embodiment the method further comprises administering zinc ions.

Moreover the present invention also relates to a method for treatment of mammals suffering from deep vein thrombosis, pulmonary embolism, stroke, disseminated intravascular coagulation (DIC), vascular restenosis, platelet deposition and associated disorders and myocardial infarction, and in the prophylactic treatment of mammals with atherosclerotic vessels at risk for thrombosis, which method comprises administering a therapeutically effective amount of a compound according to the first, second or third aspect of the invention, optionally in combination with a pharmaceutical acceptable excipient and/or carrier to the mammal in need of such a treatment. Such compound being e.g. 1-hydroxy-7-hydroxycarbamoylquinoxaline-2,3(1H, 4H)-dione or Pyrazole-3,5-dicarbohydroxamic acid. In one embodiment the method further comprises administering zinc ions.

The regimen for any patient to be treated with the compositions according to the present invention should be determined by those skilled in the art. The daily dose to be administered in therapy can be determined by a physician and will depend on the particular compound employed, on the route of administration and on the age and the condition of the patient. The daily dose comprises an effective amount (i.e. a therapeutically effective amount) of a compound according to the invention wherein the amount can be determined by a physician and will depend on the particular compound employed, on the route of administration and on the age and the condition of the patient. A convenient daily dosage can be in the range of from about 0.1 µmol to about 0.2 mmol of the active ingredient.

The pharmaceutical composition according to the fourth aspect of the invention may be useful for modulating and normalizing an impaired haemostatic balance in a mammal. In particular, the pharmaceutical composition may be useful for the treatment of coagulation-related diseased states. More particularly the pharmaceutical composition may be useful as an inhibitor of blood coagulation in a mammal, as an inhibitor of clotting activity in a mammal, as an inhibitor of deposition of fibrin in a mammal, as an inhibitor of platelet deposition in a mammal, in the treatment of mammals suffering from deep vein thrombosis, pulmonary embolism, stroke, disseminated intravascular coagulation (DIC), vascular restenosis, platelet deposition and associated disorders and myocardial infarction, and in the prophylactic treatment of mammals with atherosclerotic vessels at risk for thrombosis.

In a seventh aspect the invention relates to a pharmaceutical composition comprising a compound of the general formula Ia $$M^1\diagdown_{(Y^1)_p}\diagup^{(A)_a}\diagdown_{(Y^2)_s}\diagup^{M^2} \quad (Ia)$$

wherein
$M^1$ is heteroaryl, a group of the formula $$Z^1-\underset{\underset{N}{|}}{\overset{\overset{Z^3}{|}}{N}}-\overset{\overset{O}{\|}}{C_1}-,$$

or a group of the formula $$Z^5-\overset{N-OH}{\|\|}\overset{O}{\underset{C_1}{\|}}-,$$

$M^2$ is heteroaryl, or a group of the formula $$-\overset{\overset{O}{\|}}{C_2}-\underset{\underset{Z^4}{|}}{\overset{\overset{Z^2}{|}}{N}}-Z^4,$$

or a group of the formula $$Z^6-\overset{N-OH}{\|\|}\overset{O}{\underset{C_2}{\|}}-,$$

$Z^1$, $Z^2$, $Z^3$ and $Z^4$ independently of each other are hydrogen, $C_{1-4}$alkyl, hydroxy, amino or a valence bond attached to A, $Z^5$ and $Z^6$ represent a >C=O, which is attached to A, $Y^1$ and $Y^2$ independently of each other are a group of the formula $-X^1\sim X^2\sim X^3-$, wherein ~independently of each other means a single or double bond, and $X^1$ represents >C=O, >CHR$^5$, >CH$_2$, >CH— or a valence bond, wherein R$^5$ is hydrogen, $C_{1-4}$alkyl, amino, $C_{1-4}$alkylamino, or di($C_{1-4}$alkyl)amino, $X^2$ represents —NH—, >N—, >CH$_2$ or >CH—, and $X^3$ represents —S—, >CH$_2$, >CH— or a valence bond, A is aryl or heteroaryl, p, a and s independently of each other are 0 or 1;

or a pharmaceutically acceptable salt thereof;

with the provisos that a+p+s is at least 1; in combination with a pharmaceutical acceptable excipient and/or carrier.

In one embodiment of the above compound of general formula Ia $M^1$ and $M^2$ are independently of each other pyridinyl, such as pyridin-2-yl. In a preferred embodiment only one of $M^1$ and $M^2$ are pyridinyl, such as pyridin-2-yl.

In a second embodiment of the above compound of general formula Ia $M^1$ is a group of the formula $$Z^1-\underset{\underset{N}{|}}{\overset{\overset{Z^3}{|}}{N}}-\overset{\overset{O}{\|}}{C_1}-,$$

wherein $Z^1$ and $Z^3$ independently of each other are as defined above, or a group of the formula $$Z^5-\overset{N-OH}{\|\|}\overset{O}{\underset{C_1}{\|}}-,$$

wherein $Z^5$ is a >C=O attached to A.

In a third embodiment of the above compound of general formula Ia $M^2$ is a group of the formula $$-\overset{O}{\underset{\|}{C_2}}-\overset{Z^2}{\underset{|}{N}}-Z^4,$$

wherein $Z^2$ and $Z^4$ independently of each other are as defined above, or a group of the formula $$Z^6-\overset{N-OH}{\underset{\|}{\phantom{X}}}-\overset{O}{\underset{\|}{C_2}}-,$$

wherein $Z^6$ is a >C=O attached to A.

In a further embodiment of the above compound of general formula Ia, the distance between $C_1$ and $C_2$ is from about 0.37 nm to about 0.47 nm.

In a still further embodiment of the above compound of general formula Ia, the distance between $C_1$ and $C_2$ is from about 0.47 nm to about 0.57 nm.

In a further embodiment of the above compound of general formula Ia, the distance between $C_1$ and $C_2$ is from about 0.57 nm to about 0.67 nm.

In a still further embodiment of the above compound of general formula Ia, the distance between $C_1$ and $C_2$ is from about 0.67 nm to about 0.77 nm.

In a further embodiment of the above compound of general formula Ia the distance between $C_1$ and $C_2$ is from about 0.37 nm to about 0.77 nm, preferably from about 0.40 nm to about 0.70 nm, more preferred from about 0.40 nm to about 0.65 nm.

In a still further embodiment of the above compound of general formula Ia $Z^1$, $Z^2$, $Z^3$ and $Z^4$ are independently of each other hydrogen, methyl, hydroxy, amino or a valence bond attached to A. Preferably $Z^1$, $Z^2$, $Z^3$ and $Z^4$ are independently of each other hydrogen, hydroxy, amino or a valence bond attached to A.

In a further embodiment of the above compound of general formula Ia $Y^1$ and $Y^2$ are independently of each other a group of the formula $-X^1 \sim X^2 \sim X^3-$, wherein~independently of each other means a single or double bond, and $X^1$ represents >C=O, >CHR$^5$, >CH$_2$, >CH— or a valence bond, wherein R$^5$ is hydrogen, methyl, amino, methylamino, or di-methylamino, $X^2$ represents —NH—, >N—, >CH$_2$ or >CH—, and $X^3$ represents —S—, >CH$_2$, >CH— or a valence bond. Preferably $X^1$ is >C=O, >CHR$^5$ or a valence bond, wherein R$^5$ is amino, $X^2$ is —NH— or >CH$_2$ and $X^3$ is —S— or a valence bond.

In a still further embodiment of the above compound of general formula Ia A is phenyl, 1,2,3-triazolyl, 1,2,4-triazolyl, or pyrazolyl.

In a particular embodiment of the above compound of general formula Ia the compound is selected from:

1-hydroxy-7-hydroxycarbamoylquinoxaline-2,3(1H,4H)-dione, having the formula III (III)

5-(2-pyridyl)-1,2,4-triazole-3-carbohydrazide 1,2,3-triazole-4,5-dicarbohydrazide Pyrazole-3,5-dicarbohydroxamic acid 4,7-Dihydro-[4,7]phenanthroline-1,2,3,8,9,10-hexaone-2,9-dioxime L-Cystine dihydroxamate In a still further embodiment of the seventh aspect the composition further contains zinc ions. Such zinc ions may be provided via zinc salts, e.g. ZnCl$_2$ or the like.

In a further embodiment of the seventh aspect of the invention the pharmaceutical composition is administered by the oral route. However, the route of administration of the compositions containing a compound of the invention may be any route which effectively transports the active compound to its site of action, such as transdermal, pulmonal, subcutane, rectal, etc.

In a still further embodiment of the seventh aspect of the invention the pharmaceutical composition may be useful for modulating and normalizing an impaired haemostatic balance in a mammal. In particular the pharmaceutical composition may be useful for the treatment of coagulation-related diseased states.

In a further embodiment of the seventh aspect of the invention the pharmaceutical composition may be useful as an inhibitor of blood coagulation in a mammal, or as an inhibitor of clotting activity in a mammal, or as an inhibitor of deposition of fibrin in a mammal, or as an inhibitor of platelet deposition in a mammal.

In a still further embodiment of the seventh aspect of the invention the pharmaceutical composition may be useful in the treatment of mammals suffering from deep vein thrombosis, pulmonary embolism, stroke, disseminated intravascular coagulation (DIC), vascular restenosis, platelet deposition and associated disorders and myocardial infarction, and in the prophylactic treatment of mammals with atherosclerotic vessels at risk for thrombosis.

Furthermore the present invention relates to the use of a compound of the general formula Ia

 (Ia)

wherein
$M^1$ is heteroaryl, a group of the formula

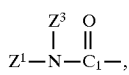

or a group of the formula

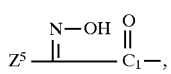

$M^2$ is heteroaryl, or a group of the formula

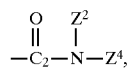

or a group of the formula

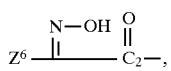

$Z^1$, $Z^2$, $Z^3$ and $Z^4$ independently of each other are hydrogen, $C_{1-4}$alkyl, such as methyl, hydroxy, amino or a valence bond attached to A,
$Z^5$ and $Z^6$ represent a >C=O, which is attached to A,
$Y^1$ and $Y^2$ independently of each other are a group of the formula $-X^1 \sim X^2 \sim X^3-$, wherein~independently of each other means a single or double bond, and $X^1$ represents >C=O, >CHR$^5$, >CH$_2$, >CH— or a valence bond, wherein $R^5$ is hydrogen, $C_{1-4}$alkyl, such as methyl, amino, $C_{1-4}$alkyl-amino, or di($C_{1-4}$alkyl)amino, $X^2$ represents —NH—, >N—, >CH$_2$ or >CH—, and $X^3$ represents —S—, >CH$_2$, >CH— or a valence bond,
A is aryl such as phenyl or heteroaryl such as pyrazolyl, 1,2,3-triazolyl, or 1,2,4-triazolyl,
p, a and s independently of each other are 0 or 1;
or a pharmaceutically acceptable salt thereof;
with the provisos that a+p+s is at least 1; in the preparation of a medicament for modulating and normalizing an impaired haemostatic balance in a mammal.

Also the compound of formula Ia may be useful in the preparation of a pharmaceutical composition for treatment of coagulation-related diseased states. In particular it may be useful for the preparation of a pharmaceutical composition, for use as an inhibitor of blood coagulation in a mammal, or for use as an inhibitor of clotting activity in a mammal, or for use as an inhibitor of deposition of fibrin in a mammal, or for use as an inhibitor of platelet deposition in a mammal.

In paticular the compound of formula Ia may be useful for the preparation of a pharmaceutical composition, for treatment of mammals suffering from deep vein thrombosis, pulmonary embolism, stroke, disseminated intravascular coagulation (DIC), vascular restenosis, platelet deposition and associated disorders and myocardial infarction, and in the prophylactic treatment of mammals with atherosclerotic vessels at risk for thrombosis.

In one embodiment of the use of the compound of formula Ia for the preparation of a pharmaceutical composition, said composition further contains zinc ions.

The present invention also relates to a method of modulating and normalizing an impaired haemostatic balance in a mammal, which method comprises administering an effective amount of a compound of formula Ia, in combination with a pharmaceutical acceptable excipient and/or carrier to the mammal in need of such a treatment. Such compound of formula Ia may be selected from the compounds
1-hydroxy-7-hydroxycarbamoylquinoxaline-2,3(1H,4H)-dione,
5-(2-pyridyl)-1,2,4-triazole-3-carbohydrazide,
1,2,3-triazole-4,5-dicarbohydrazide,
Pyrazole-3,5-dicarbohydroxamic acid,
4,7-Dihydro-[4,7]phenanthroline-1,2,3,8,9,10-hexaone-2,9-dioxime, or
L-Cystine dihydroxamate.

Moreover the present invention relates to a method for treatment of coagulation-related diseased states in a mammal, which method comprises administering an effective amount of a compound of formula la, in combination with a pharmaceutical acceptable excipient and/ or carrier to the mammal in need of such a treatment.

In one embodiment the method is for treatment of mammals suffering from deep vein thrombosis, pulmonary embolism, stroke, disseminated intravascular coagulation (DIC), vascular restenosis, platelet deposition and associated disorders and myocardial infarction, and in the prophylactic treatment of mammals with atherosclerotic vessels at risk for thrombosis, which method comprises administering a therapeutically effective amount of a compound of formula Ia, in combination with a pharmaceutical acceptable excipient and/or carrier to the mammal in need of such a treatment.

In another embodiment the method further comprises administering zinc ions.

In a further aspect the present invention relates to a complex comprising a compound according to any one of the claims 1–15 or a compound of formula Ia and zinc ions. Such compound being e.g. 1-hydroxy-7-hydroxycarbamoylquinoxaline-2,3(1H,4H)-dione or pyrazole-3,5-dicarbohydroxamic acid.

In one embodiment of the complex of the invention it may be useful for modulating and normalizing an impaired haemostatic balance in a mammal. In particular it may be useful for the treatment of coagulation-related diseased states.

In another embodiment of the complex of the invention it may be useful as an inhibitor of blood coagulation in a mammal, or as an inhibitor of clotting activity in a mammal, or as an inhibitor of deposition of fibrin in a mammal, or as an inhibitor of platelet deposition in a mammal.

In a further embodiment of the complex of the invention it may be useful in the treatment of mammals suffering from deep vein thrombosis, pulmonary embolism, stroke, disseminated intravascular coagulation (DIC), vascular restenosis, platelet deposition and associated disorders and myocardial infarction, and in the prophylactic treatment of mammals with atherosclerotic vessels at risk for thrombosis.

Furthermore the invention relates to a method for inhibiting tissue factor activity in a mammal which method comprises administering an effective amount of a compound according to any one of claims 1–15 or a compound of formula la, in combination with a pharmaceutical acceptable excipient and/ or carrier to the mammal in need of such a treatment. One embodiment hereof further comprises administering zinc ions.

In a further aspect the invention relates to a method for inhibiting factor VII activity by substantially reducing the ability of activated factor VII to catalyze tissue factor-enhanced activation of factors X and IX comprising administering a compound according to any one of the claims 1–15 or a compound of formula Ia, in combination with a pharmaceutical acceptable excipient and/or carrier to a mammal in need of such a treatment. One embodiment hereof further comprises administering zinc ions.

The invention also relates to a method for substantially inhibiting the binding of FVII to tissue factor comprising replacing FVII-bound calcium ions with zinc ions, which method comprises administering an effective amount of a compound according to any one of claims 1–15 or a compound of formula Ia, in combination with a pharmaceutical acceptable excipient and/or carrier to the mammal in need of such a treatment. One embodiment hereof further comprises administering zinc ions.

The invention also concerns a method of detecting a zinc chelator which potentiates zinc ion inhibition of factor VIIa or factor VIIa/tissue factor activity, comprising testing one or more specific compounds in the assay disclosed in example 4. Such compound may be selected from compounds of formula Ia or Ib, or from any compound of non-peptide origin.

The invention also relates to a method of substantially reducing the binding of FVII to tissue factor by replacing FVII-bound $Ca^{2+}$ with $Zn^{2+}$, and the use of a $Ca^{2+}$ binding site in FVII to substantially reduce the binding of FVII to tissue factor.

The compositions of the invention are particularly useful in methods for treating patients when formulated into pharmaceutical compositions, where they may be given by oral administration to individuals suffering from a variety of diseased states to treat coagulation-related conditions.

Among the medical indications for the subject compositions are those commonly treated with anticoagulants, such as, for example, deep vein thrombosis, pulmonary embolism, stroke, disseminated intravascular coagulation (DIC) and myocardial infarction. With an oral administration, the compositions of the invention is particular useful in prophylactic treatment of patients with atherosclerotic vessels at risk for thrombosis. The compositions can also be used to inhibit vascular restenosis and platelet deposition and associated disorders.

Typically for oral administration to humans the pharmaceutical compositions will comprise one or more compounds of the invention, optionally in combination with zinc salts, and pharmaceutically acceptable carriers and buffers.

Examples of pharmaceutically acceptable salts are pharmaceutically acceptable acid addition salts with non-toxic acids, either inorganic acids such as hydrochloric acid, sulphuric acid and phosphoric acid, or organic acids such as formic acid, acetic acid, propionic acid, succinic acid, gluconic acid, lactic acid, citric acid, ascorbic acid, benzoic acid, embonic acid, methanesulphonic acid and malonic acid.

The compounds of formula Ia and/or Ib are prepared by methods known per se by the skilled art worker, such as exemplified by the preparation of compound III in example No. 1.

This invention further provides pharmaceutical compositions which comprise at least one compound of formula I or a pharmaceutically acceptable acid addition salt thereof in connection with a pharmaceutically acceptable carrier. Such compositions may be in the form of powders, solutions, or suspensions, which may or may not be divided in unit dosage form or in the form of capsules or tablets. A preferred composition is in the form of an composition for oral administering.

The pharmaceutical compositions of this invention may comprise carriers, diluents, absorption enhancers, tablet disintegrating agents and other ingredients which are conventionally used in the art. The powders and tablets preferably contain from 5 to 99%, more preferred from 10 to 90 of the active ingredient. Examples of solid carriers are magnesium carbonate, magnesium stearate, dextrin, lactose, sugar, talc, gelatin, pectin, tragacanth, methyl cellulose, sodium carboxymethyl cellulose, low melting waxes and cocoa butter. Liquid compositions include sterile solutions, suspensions and emulsions suitable for parenteral injection.

The compositions of this invention are prepared by methods known per se by the skilled art worker.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

The following compounds are commercially available:

5-(2-pyridyl)-1,2,4-triazole-3-carbohydrazide (obtained from Maybridge Chemicals LTD (SEW 00446))

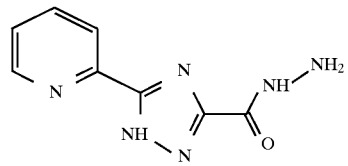

1,2,3-triazole-4,5-dicarbohydrazide (obtained from Odense University; is also disclosed in Farmaco, 50,(2) 1995, 99–106)

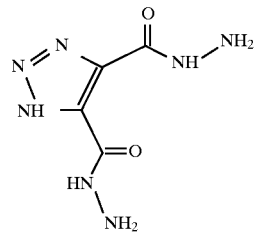

4,7-Dihydro-[4,7]phenanthroline-1,2,3,8,9,10-hexaone-2,9-dioxime (obtained from Labotest under the number (LT-2 AM36))

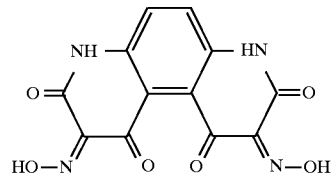

Example 1

Preparation of 1-Hydroxy-7-hydroxycarbamoylquinoxaline-2,3(1H,4H)-dione:

a) 4-Ethoxalylamino-3-nitrobenzoic acid

Anhydrous triethylamine (22.6 ml, 0.162 mol) was added to a solution of 4-amino-3-nitrobenzoic acid (14.4 g, 0.081 mol) in a mixture of dry tetrahydrofuran (300 ml) and dry N,N-dimethylformamide (100 ml). Then a solution of ethyl oxalylchloride (18 ml, 0.162 mol) in 100 ml of dry tetrahydrofuran was added dropwise at 0° C. The mixture was stirred overnight at room temperature and triethylamine hydrochloride was removed by filtration. The filtrate was evaporated to dryness and the residue was triturated with water. The crude product was isolated by filtration and recrystallised from ethanol to give 14.4 g of the title compound which was used without further purification in the subsequent reductive cyclisation reaction. $^1$H-NMR (DMSO-d$_6$): 1.35 (t, J=7 Hz, 3H, CH$_3$), 4.36 (q, J=7 Hz, 2H, CH$_2$), 8.2–8.6 (m, 3H, ArH), 11.6 (s, 1H, NH).

b) 7-Carboxy-1-hydroxyquinoxaline-2,3(1 H,4H)-dione

A solution of 4-ethoxalylamino-3-nitrobenzoic acid (14.0 g, 49.6 mmol) in 800 ml of N,N-dimethylformamide was hydrogenated at room temperature and atmospheric pressure in the presence of 1.3 g of 5% platinum on carbon for 2.5 h. The catalyst was filtered off and washed with N,N-dimethylformamide. The filtrate was evaporated to dryness and the residue was triturated with 500 ml of water and filtered. The crude product was dissolved in 900 ml of 1M potassium dihydrogen phosphate buffer (pH 7.4), filtered and reprecipitated with 6M hydrochloric acid to yield 7.7 g (70%) of the title compound. $^1$H-NMR (DMSO-d$_6$): 7.25 (d, J=9 Hz, 1H, ArH), 7.75 (dd, J=9 Hz, 2 Hz, 1H, ArH), 7.98 (d, J=2 Hz, 1H, ArH), 12.3 (br.s, 1H, exchangeable).

c) 1-Benzyloxy-7-carboxyquinoxaline-2,3(1H,4H)-dione

7-Carboxy-1-hydroxyquinoxaline-2,3(1H,4H)-dione (2.22 g, 10 mmol) was dissolved in a mixture of 50 ml of 1M potassium dihydrogen phosphate buffer (pH 7.4) and 25 ml of ethanol by gently heating. To the cooled mixture was added 1.19 ml (10 mmol) of benzylbromide and the mixture was stirred overnight at room temperature. The precipitate was isolated by filtration and washed with ethanol. The crude product was triturated with 4M hydrochloric acid and washed with water and dried in vacuo to give 1.56 g (50%) of the title compound. $^1$H-NMR (DMSO-d$_6$): 5.22 (s, 2H, CH$_2$), 7.2–7.9 (m, 8H, ArH), 12.35 (s, 1H, exchangeable), 13.05 (br.s, 1H, exchangeable).

d) 1-Benzyloxy-7-(benzyloxycarbamoyl)quinoxaline-2,3 (1H,4H)-dione

To an ice-cooled solution of 1-Benzyloxy-7-carboxyquinoxaline-2,3(1H,4H)-dione (422 mg, 1.35 mmol) in 10 ml of N,N-dimethylformamide was added 1-hydroxybenzotriazole (218 mg, 1.48 mmol) followed by 1-(3-dimethylaminopropyl)-3-ethylcarbodiimide hydrochloride (272 mg, 1.42 mmol). Stirring was continued for 30 min at 0° C. and O-benzylhydroxylamine hydrochloride (237 mg, 1.49 mmol) and dry triethylamine (0.21 ml, 1.5 mmol) was added. The mixture was stirred overnight at room temperature, then cooled and filtered. The isolated solid was successively washed with water, saturated aqueous sodium hydrogen carbonate and water. Recrystallisation from ethanol gave 290 mg (51%) of the title compound. $^1$H-NMR (DMSO-d$_6$): 4.95 (s, 2H, CH$_2$), 5.19 (s, 2H, CH$_2$), 7.2–7.8 (m, 13H, ArH), 11.8 (br.s, 1H, exchangeable), 12.3 (br.s, 1H, exchangeable).

e) 1-Hydroxy-7-hydroxycarbamoylquinoxaline-2,3(1H, 4H)-dione

A suspension of 1-Benzyloxy-7-(benzyloxycarbamoyl) quinoxaline-2,3(1H,4H)-dione (250 mg, 0.6 mmol) in 50 ml of ethanol was hydrogenated at atmospheric pressure and room temperature for 1 h in the presence of 50 mg of 5% palladium on carbon. Water (20 ml) and 4 ml of 2N sodium hydroxide was added to dissolve the product and the catalyst was removed by filtration. The filtrate was acidified with 4 ml of 4M hydrochloric acid, evaporated to about 10 ml and filtered to give a white solid. Washing with a small amount of cold water and ethanol yielded 109 mg (70%) of the title compound. $^1$H-NMR (DMSO-d$_6$): 7.21 (d, J=8 Hz,1H, ArH), 7.60 (dd, J=8 Hz, 2 Hz, 1H, ArH), 7.90 (d, J=2 Hz, 1H, ArH), 9.05 (br.s, 1H, exchangeable), 11.35 (br.s, 1H, exchangeable), 11.82 (br.s, 1H, exchangeable), 12.35 (br.s, 1H, exchangeable).

Example 2

Synthesis of pyrazole-3,5-dicarbohydroxamic acid (28–3028) on solid phase:

a) Synthesis of the linkage[1]: a) Sasrin® resin (10.0 g, 0.73 mmol/g) was swelled in dichloromethane (40 mL) and diisopropylethylamine (40 mL), and cooled to 0° C. A solution of methanesulfonyl chloride (5.0 mL, 7.40 g, 64.6 mmol) in dichloromethane (20 mL) was added dropwise while stirring under argon, and stirring was continued for 30 min at 0° C. and for 45 min at 25° C. Subsequently, the resin was drained and washed with dichloromethane (3 portions of 80 mL) and N-methylpyrrolidinone (NMP; 3 portions of 80 mL). b) In a 500 mL flask equipped with a mechanical stirrer, N-hydroxyphthalimide (23.8 g, 146 mmol) was dissolved in NMP (280 mL), and cesiun carbonate (27.7 g, 73 mmol) was added. The mesylated resin was added in small portions at 25° C., and stirring was continued for 30 min at 25° C. and for 16 h at 80° C. The chocolate-brown reaction mixture was poured into a Buchner funnel and washed extensively with methanol, water, methanol, dichloromethane, until the resin was colorless. c) The resin was suspended in ethanol (70 mL), anhydrous hydrazine (8 mL) was added, and the mixture was shaken at 25° C. for 16 h. The resin was washed extensively with methanol, dichloromethane, methanol and dried; yield 9.50 g (95%).

b) Attachment of pyrrole-3,5-dicarboxylic acid to the resin prepared above: 0.10 g of the resin synthesized above was washed with N-methylpyrrolidone (1.5 mL). Subsequently, pyrrole-3,5-dicarboxylic acid (155 mg, 1.0 mmol), NMP (0.90 mL), 4-N,N-dimethylaminopyridine (20 mg) in NMP (0.10 mL) and diisopropylcarbodiimide (78 $\mu$L, 0.5 mmol) were added, and the mixture was shaken at r.t. for 120 min. Subsequently, the mixture was washed with NMP (4 portions of 2 mL).

c) A solution of PyBOP® (0.5 mmol, 260 mg) in NMP (250 $\mu$L) was added to the resin. To this, a solution of hydroxylamine hydrochloride (70 mg, 1 mmol) in NMP (0.80 mL)/N-methylmorpholine (0.20 mL) was added, and the mixture was shaken at r.t. for 30 min. Subsequently, the resin was washed with dimethylformamide (3 portions of 2 mL) and dichloroethane (5 portions of 2 mL).

d) Cleavage: The resin was washed with dichloroethane (2 mL), and a mixture of 25% trifluoroacetic acid in dichloroethane (1.0 mL) was added. The mixture was shaken at r.t. for 15 min. The resin was filtered, the filtrate was collected, and the resin was washed with acetonitrile (2 portions of 0.80 mL). The solvents were evaporated in vacuo, and the crude samples were submitted to assay.

Lit.: L. S. Richter, M. C. Desai, *Tetrahedron Lett.* 1997, 38, 321.

Example 3

Demonstration of competition between the stimulatory effect of $Ca^{2+}$ on factor VIIa activity and the inhibiratory effect of $Zn^{2+}$.

Preveous studies (Pedersen et al. *Thromb. Haemostas.* 65: 528–534 (1991)) resulted in a putative model for Zn inhibition of factor VIIa which suggested that $Zn^{2+}$ ions bind to a site involving His 241 (adjacent to the active site Asp 242) in factor VIIa. An effect of $Ca^{2+}$ ions is not easily contemplated in this model since the binding site for $Ca^{2+}$ in the serine protease domain is not nearby. It was therefore surprising when we observed (FIG. 1A and 1B) that the inhibitory effect of $Zn^{2+}$ was partly abolished by $Ca^{2+}$ ions in a competitive manner. This effect was observed with factor VIIa in the absence (FIG. 1A) as well as in the presence (FIG. 1B) of tissue factor. We interpret these result to mean that $Zn^{2+}$ ions are more likely to interact with residues in immeadiate contact with the $Ca^{2+}$-binding site comprising the surface loop residues 210–220 of the factor VIIa serine protease domain (Wildgoose et al. *Biochemistry* 32: 114–119 (1993)). Since histidines are prominant in zinc coordination we further propose that one or more of the residues of His 211, His 216 and His 256 are involved in the binding of $Zn^{2+}$ ions to factor VIIa.

TABLE 1

|  | No $ZnCl_2$ | Factor VIIa/tissue factor activity (%) 100 μM $ZnCl_2$ |
| --- | --- | --- |
| Control | 100 | 65 |
| 50 μM NNC (28) | 98 | 55 |
| 50 μM NNC (67) | 94 | 52 |
| 50 μM NNC (30) | 99 | 56 |
| 50 μM NNC (54) | 98 | 42 |

The activity of 10 nM FVIIa and 50 nM tissue factor in the presence and absence of Zn and chelator was measured with S2288 as described in Example 4

We claim:

1. A compound of the general formula Ia $$M^1 \diagdown_{(Y^1)_p} \diagup^{(A)_a} \diagdown_{(Y^2)_s} \diagup M^2 \quad (Ia)$$

Wherein

M' is quinoxaline or a group of the formula $$Z^1-N-C_1-, \text{ with } Z^3 \text{ above N and O above } C_1$$

or a group of the formula, $$Z^5 \overset{N-OH}{=} \overset{O}{=} C_1-$$

$M^2$ is quinoxaline or a group of the formula $$-C_2-N-Z^4, \text{ with O above } C_2 \text{ and } Z^2 \text{ above N}$$

or a group of the formula $$Z^6 \overset{N-OH}{=} \overset{O}{=} C_2-$$

$Z^1$, $Z^2$, $Z^3$, and $Z^4$, independently of each other are hydrogen, with the proviso that $Z^1$ and $Z^3$, and $Z^2$ and $Z^4$, respectively are not both hydrogen; $C_{1-4}$ alkyl, hydroxy, or a valence bond attached to A, $Z^5$ and $Z^6$ represent a >C=O, which is attached to A, $Y^1$ and $Y^2$ independently of each other are a group of the formula $-X^1 \sim X^2 \sim X^3-$, wherein~independently of each other means a single or double bond, and $X^1$ represents >C=O, >$CHR^5$, >$CH_2$, >CH— or a valence bond, wherein $R^5$ is hydrogen, $C_{1-4}$alkyl, amino, $C_{1-4}$ alkyl-amino, or di($C_{1-4}$ alkyl) amino, $X^2$ represents —NH—, >N—, >$CH_2$ or >CH— and $X^3$ represents —S—, >$CH_2$, >CH— or a valence bond, A is aryl or quinoxaline, p, a and s independently of each other are 0 or 1;

with the provisos that a+p+s is at least 1 and pharmaceutically acceptable salts thereof.

2. The compound according to claim 1, in which said compound is 1-hydroxy-7-hydroxycarbamoylquinoxaline-2,3(1H,4H)-dione.

3. A compound of the general formula Ib

[structure diagram with H, OH, N, C1, R1, N1, OH, O, C2, R2, C3, X]

Wherein

X is a chain, aliphatic or comprising hetero atoms as chain members; and R1 is hydrogen, a substituted or non-substituted amino group, or a methyl group; and R2 is hydrogen, or a methyl group; or X, in combination with C2, R1, R2, N1, and C3, forms a carbocyclic system; and wherein the distance between C1 and C3 is from about 0.37 nm to about 0.77 nm; and pharmaceutically acceptable salts thereof; with the proviso that the compound is not L-cystine dihydroxamate.

4. The compound according to claim 3, wherein the residue X is a branched or unbranched carbon chain, or X comprises chain links of carbon or nitrogen or sulphur or oxygen atoms arranged in a branched or unbranched chain and comprises single or double bonds between chain links.

5. The compound according to claim 3, wherein X in combination with C2, R1, R2, N1, and C3 form a carbocyclic system, with the proviso that the distance between the carbon atoms of hydroxamate C1 and C3 carbonyl groups is from about 0.37 nm to about 0.77 nm.

6. A pharmaceutical composition comprising the compound of claim 1 in combination with a pharmaceutically acceptable excipient or carrier.

7. The composition according to claim 6, in which said compound is 1-hydroxy-7-hydroxycarbamoylquinoxaline-2,3(1H,4H)-dione.

8. A pharmaceutical composition comprising the compound of claim 3, in combination with a pharmaceutically acceptable excipient or carrier.

9. The pharmaceutical composition of claim 6, which further contains zinc ions.

10. The pharmaceutical composition of claim 8, which further contains zinc ions.

11. A method for inhibiting blood coagulation in a mammal comprising administering to said mammal in need thereof the pharmaceutical composition of claim 6 in an amount effective to inhibit blood coagulation in said mammal.

12. A method for inhibiting blood coagulation in a mammal comprising administering to said mammal in need thereof the pharmaceutical composition of claim 8 in an amount effective to inhibit blood coagulation in said mammal.

13. A method for modulating and normalizing an impaired haemostatic balance in a mammal in need thereof comprising administering the composition of claim 6 in an amount effective to modulate and normalize impaired haemostatic balance in said mammal.

14. A method for modulating and normalizing an impaired haemostatic balance in a mammal in need thereof comprising administering the composition of claim 8 in an amount effective to modulate and normalize impaired haemostatic balance in said mammal.

15. A method for substantially reducing the ability of activated factor VII to catalyze tissue factor-enhanced activation of factors X and IX in a mammal in need thereof comprising administering the composition of claim 6 in an amount effective to catalyze tissue factor-enhanced activation of factors X and IX in said mammal.

16. A method for substantially reducing the ability of activated factor VII to catalyze tissue factor-enhanced activation of factors X and IX in a mammal in need thereof comprising administering the composition of claim 8 in an amount effective to catalyze tissue factor-enhanced activation of factors X and IX in said mammal.

17. A method for substantially inhibiting the binding of factor VII to tissue factor in a mammal in need thereof, comprising administering the composition of claim 6 in an amount effective to inhibit the binding of factor VII to tissue factor in said mammal.

18. A method for substantially inhibiting the binding of factor VII to tissue factor in a mammal in need thereof, comprising administering the composition of claim 8 an amount effective to inhibit the binding of factor VII to tissue factor in said mammal.

19. A method for the treatment of a mammal suffering from deep vein thrombosis, pulmonary embolism, stroke, disseminated intravascular coagulation vascular restenosis, platelet deposition and associated disorders or myocardial infarction, or in the prophylactic treatment of mammals with atherosclerotic vessels at risk for thrombosis, comprising administering to said mammal in need thereof, a therapeutically effective amount of the composition of claim 6.

20. A method for the treatment of a mammal suffering from deep vein thrombosis, pulmonary embolism, stroke, disseminated intravascular coagulation, vascular restenosis, platelet deposition and associated disorders or myocardial infarction, or in the prophylactic treatment of mammals with atherosclerotic vessels at risk for thrombosis, comprising administering to said mammal in need thereof, a therapeutically effective amount of the composition of claim 8.

* * * * *